United States Patent [19]

Seiler et al.

[11] Patent Number: 4,537,983

[45] Date of Patent: Aug. 27, 1985

[54] METHOD OF PREPARING 2-PHENYLETHYLCHLOROSILANES

[75] Inventors: Claus-Dietrich Seiler, Rheinfelden; Hans-Joachim Vahlensieck, Wehr, both of Fed. Rep. of Germany

[73] Assignee: Dynamit Nobel AG, Cologne, Fed. Rep. of Germany

[21] Appl. No.: 644,808

[22] Filed: Aug. 27, 1984

[30] Foreign Application Priority Data

Sep. 2, 1983 [DE] Fed. Rep. of Germany ....... 3331682

[51] Int. Cl.$^3$ ................................................. C07F 7/08
[52] U.S. Cl. .................................................... 556/479
[58] Field of Search ......................................... 556/479

[56] References Cited

U.S. PATENT DOCUMENTS 3,925,434 12/1975 Chuang ............................. 556/479 X
4,469,881 9/1984 Arkles ............................... 556/479 X

*Primary Examiner*—Paul F. Shaver
*Attorney, Agent, or Firm*—Felfe & Lynch

[57] ABSTRACT

The present invention relates to a method of preparing 2-phenylethylchlorosilanes. Hydrogen chlorosilanes and styrene are used as starting products, and they are reacted together in the presence of benzothiazole. Benzothiazole is used at least in the same amount as the platinum catalyst. The preferred molar ratio of platinum catalyst to benzothiazole is between 1:2 and 1:50. The reaction can be performed with high yields of the 2-isomer, which is virtually free of the 1-isomer, at temperatures up to about 90° C. At the same time, an excess pressure of up to 6 bar is easily tolerable without marked reduction of the yields of the desired product.

10 Claims, No Drawings

METHOD OF PREPARING 2-PHENYLETHYLCHLOROSILANES

BACKGROUND OF THE INVENTION

The subject matter of the present invention is a method of preparing 2-phenylethylchlorosilanes in which hydrogen chlorosilanes are added onto styrene in the presence of platinum catalysts. The process suppresses the formation of the 1-phenylethyl compounds.

The addition of unsaturated organic compounds onto silicon compounds having one or two Si-H bonds in the presence of platinum catalysts is generally known (cf. J. Am. Ch. Soc. 79, 1957 pp. 974–979). In this reaction, also known as an addition reaction, when unsaturated organic compounds having multiple terminal bonds are used, the silyl moiety is mostly added onto the terminal carbon atom; however, to a more or less great extent an addition of the silyl moiety onto the adjacent carbon atom takes place, reducing the yields of the compound that is mainly desired, which contains the silyl moiety in the terminal position.

In the reaction of styrene with Si-H compounds, there is also the circumstance that, under the reaction conditions, a partial polymerization of the styrene to polystyrene easily takes place, which again reduces the yield of phenylethyl silanes. This tendency to polymerize is especially great when platinum compounds are used on active carbon as the support material.

It is for this reason that a number of attempts to avoid these problems have been described. However, any heterogeneous systems in which the formation of undesired 1-phenylethyl silane is suppressed, still have the disadvantage of an excessive formation of styrene polymers.

On the other hand, the procedures in which the formation of styrene polymers is suppressed, such as for example the use of platinum or rhodium complex compounds as catalysts and/or the use of certain solvents, have not as yet offered a satisfactory solution of the problems described.

In German Pat. No. 2,602,171, the addition of phenothiazine and other nitrogenous compounds to the reaction mixture to serve as promoters of the addition reaction has been described; it is stated therein that, when this compound is used in the reaction of styrene with trichlorosilane, the beta addition product (i.e., 2-phenylethyltrichlorosilane) is formed exclusively, so that the method described therein seems to offer a solution of the problems.

This exclusive formation of 2-phenylethyltrichlorosilane, however, is accomplished only if low temperatures and low transformation rates are used. If, however, this procedure is performed at temperatures upward of about 50° C., again considerable amounts of 1-phenylethyltrichlorosilane are obtained, especially when high rates of input are used, such as are necessary for technical purposes to achieve large yields per unit of time.

The problem therefore existed of managing the platinum-catalyzed addition of hydrogen chlorosilanes onto styrene such that the formation of 1-phenylethylchlorosilanes and polymers of styrene will be suppressed, even when the reaction is performed at temperatures up to 100° C. at high rates of throughput of the starting products.

THE INVENTION

As a solution to this problem, a method has been discovered for the preparation of 2-phenylethylchlorosilanes by the addition of hydrogen chlorosilanes onto styrene in homogeneous systems, in the presence of platinum catalysts, which is characterized by performing the reaction in the presence of benzothiazole.

When the method of the invention is used, virtually naught but the desired 2-phenylethylchlorosilane is obtained, and the yield based on styrene input is greater than 90%. In the preferred embodiments, the yields based on styrene input come to even more than 98%. These good results are obtained even when the reaction is performed at elevated temperatures up to about 100° C., and even when an effort is made to achieve high volume/time yields for technical-scale production, so that, for example, more than 10 moles (approx. 1.15 liters) of styrene can be reacted per hour and per 100 moles of $HSiCl_3$ input.

The amount of benzothiazole to be used can vary greatly. The amount of the platinum catalyst can serve as a guide. The amount of benzothiazole should be at least the same as the amount of platinum catalyst on a molar basis. The preferred molar ratio of platinum catalyst to benzothiazole is between 1:2 and 1:50. Larger amounts are basically possible, but appear to offer no greater advantages.

The platinum catalyst is used in amounts which are known in themselves. In the case of pure starting substances, the catalyst can be used in amounts of $10^{-8}$ mole per mole of styrene. In general, however, it is used in amounts between $10^{-7}$ and $10^{-3}$ per mole of styrene. The preferred range is between $1 \times 10^{-6}$ and $1 \times 10^{-5}$ moles per mole of styrene.

The preferred platinum catalyst is $H_2PtCl_6$. However, any other platinum compounds known to be usable for the addition reaction can serve if they are soluble in the reaction mixture, especially in the hydrogen chlorosilane. The catalyst itself is added in a homogeneous solution, preferably in acetone.

The procedure of the invention is best performed at temperatures between 40° and 90° C. The preferred temperature range is between 65° and 75° C. At temperatures above 90° C., small amounts of 1-phenylethylchlorosilanes may form if too little benzothiazole is used.

To avoid the presence of solvents during the reaction, the procedure is performed in the higher temperature range, preferably at the excess pressure that establishes itself and can amount to between 2 and 6 bar. Basically, however, it is also possible to make the addition reaction run at standard pressure. Then, however, at temperatures above the boiling point of the hydrogen chlorosilanes, it is necessary to operate in the presence inert solvent having a boiling point below 100° C., this increases the boiling range of the system and the reaction can run in the preferred temperature range.

The preferred hydrogen chlorosilane component is trichlorosilane. The hydrogen chlorosilane, however, can also be, for example, hydrogen methyldichlorosilane, hydrogen alkyl dichlorosilanes having 2 to 8 carbon atoms in the alkyl group, or dihydrogendichlorosilane.

The process can be performed continuously or discontinuously. In the case of the discontinuous procedure, it is desirable to place the hydrogen chlorosilane in the reactor and inject styrene into it at the rate necessary for the desired volume/time yield. The catalyst and the benzothiazole are preferably contained in the hydrogen chlorosilane in that case.

In a continuous procedure, for example, the reaction components are fed into a tubular reactor in which the reactants are heated to the desired reaction temperature. The residence time of the reactants in the reactor can be selected such that volume/time yields corresponding to the discontinuous procedure are obtained.

Both in the continuous and in the discontinuous process, the reaction products are worked up in a manner known in itself, preferably by fractional distillation of the 2-phenylethyl chlorosilane.

2-Phenylethyl chlorosilanes, especially 2-phenylethyltrichlorosilane, are technically important known intermediates in the preparation of anticorrosive agents. They are also used for the modification of silicones.

EXAMPLES

The following Examples 1 to 4 are all performed in an apparatus of the following construction: a steel still of a capacity of about 30 liters, which can be heated with water of the desired temperature through a heater insert, is connected by a steel pipe to a tubular condenser (surface area approx. 1 m$^2$) situated above the still. From the bottom of the condenser a tube leads downwardly to a tube bent into a siphon (diam. 20 mm) leading into the still cover. The still itself is equipped with a pressure gauge and a temperature gauge, and has a pipeline for injecting the starting products through a pressure pump. The condenser is operated with water as the coolant.

In each of the following Examples 1 to 4, 13,500 g (100 mol) of trichlorosilane, to which 5 ml of a solution of 1 g of platinum hydrochloric acid ($H_2PtCl_6 \times 6H_2O$) in 19 ml of acetone ($=94.5$ mg$=4.8 \times 10^{-4}$ mol) has been added, is placed in the still. The catalyst amounts to about 4.33 parts of platinum per million parts of the sum of the reactants. By feeding hot water through the coils of the heater insert the system is heated to about 70° C., thus establishing an internal pressure of 3.2 bar. Condensation of the trichlorosilane vapors begins in the tubular condenser above the still. The condensates are returned to the still through the siphon. After condensation begins, 8320 g of styrene (80 mol=9.2 l) is injected into the still through a pressure pump at varying rates. After this amount has been introduced, the system is then cooled down and the reaction product is withdrawn. The reaction product is then tested by gas chromatography for its content of 1-phenylethyltrichlorosilane (in percent of chromatogram area). Then the two isomers are distilled out and the yield with respect to the styrene input is determined.

EXAMPLE 1

The general procedure described above is performed without the addition of a promoter, at a feed rate of 2 liters of styrene per hour. The results appear in Table 1.

EXAMPLE 2

The general procedure of Example 1 is performed with the addition of various amounts of phenothiazine. 370 mg, 1000, and 10,000 mg of phenothiazine are used respectively. At the stated feed rate, percentages between 2.5 and 11% of 1-phenylethyltrichlorosilane are obtained in the resultant mixture of the two isomers. The detailed results are given in Table 1 listing tests performed with the various amounts of phenothiazine under 2a to 2c.

EXAMPLE 3

The procedure of Example 2 is repeated, except that, instead of the phenothiazine, different amounts of benzothiazole, listed in Table 1, are used. Even when only 22×10 mol of benzothiazole (=1.4 ppm with respect to the reactants) is used, there are no more than negligible amounts of the 1-isomer in the reaction product. The yield with respect to input styrene even at these small amounts is greater than those achieved with phenothiazine when the latter is used in amounts that are about two powers of ten higher. The individual results are listed in Table 1.

For reasons of comparison, benzothiazole is referred to in the table as "promoter"; the stated parts per million (ppm) relates to the total of the two reactants. The percentage of the 1-isomer is the percentage of 1-phenylethyltrichlorosilane in the obtained mixture of 1-phenylethyltrichlorosilane and 2-phenylethyltrichlorosilane. The yield includes both isomers.

TABLE 1

| Example No. | Promoter | mg | ppm | Rate of injection l/h | Percentage of the 1-isomer | Yield with respect to styrene |
|---|---|---|---|---|---|---|
| 1 | — | — | — | 2 | 21.6 | 76.4 |
| 2 a | Phenothiazine | 370 | 17 | 2 | 11.4 | 85.1 |
| b | " | 1000 | 45.8 | 2 | 7.9 | 87.1 |
| c | " | 10,000 | 458 | 2 | 5.3 | 89.3 |
| 3 a | Benzothiazole | 30 | 1.4 | 2 | 0.15 | 90.1 |
| b | " | 100 | 4.36 | 2 | | |
| c | " | 250 | 11.4 | 2 | not detectable | 98.9 |
| d | " | 1000 | 45.8 | 2 | not detectable | 99.8 |
| e | " | 3000 | 137.4 | 2 | not detectable | 99.0 |

EXAMPLE 4

The procedure of Example 3 was repeated except that the throughput of the styrene was increased to 4 liters per hour. Also, the input amounts of benzothiazole were varied. The results are given in Table 2.

TABLE 2

| Benzothiazole | | Percentage 1-isomer | Yield |
|---|---|---|---|
| mg | ppm | % of area | % |
| 30 | 1.4 | 0.4 | 89.1 |
| 2500 | 11.4 | 0.01 | 98.2 |
| 1000 | 45.8 | 0.01 | 97.9 |

TABLE 2-continued

| Benzothiazole | | Percentage 1-isomer | Yield |
|---|---|---|---|
| mg | ppm | % of area | % |
| 3000 | 137.4 | 0.01 | 98.6 |

For comparison, the reaction was performed under the same conditions in the presence of 1000 mg (=45.8 ppm with respect to the reactants) of phenothiazine instead of benzothiazole. The raw product obtained had a content of 7.9 area-percent of 1-phenylethyltrichlorosilane; the yield of the two isomers amounted to only 87.1% of the styrene input.

EXAMPLE 5

In an apparatus of a construction similar to the one used in the preceding examples, but of correspondingly larger size (capacity of the still approx. 3500 l), 1755 kg of trichlorosilane was placed in the still together with 40 g of benzothiazole and 38 g of platinum hydrochloric acid and dissolved in 720 ml of acetone. The amount of liquid in the apparatus is heated to about 72° C., causing the internal pressure to establish itself at about 3.5 bar. Over a period of 6 hours, 1200 liters of styrene are injected with a pressure pump while the temperature rises slightly. After a post-reaction period of time, a sample is taken from the reaction mixture and tested by gas chromatography. No content of 1-phenylethertrichloro-silane plus 2-phenylethyltrichlorosilane is detectable.

The reaction mixture is then distilled. The yield of 2-phenylethyltrichlorosilane amounts to 96.7% of the input styrene.

It will be understood that the specification and examples are illustrative but not limitative of the present invention and that other embodiments within the spirit and scope of the invention will suggest themselves to those skilled in the art.

We claim:

1. method of preparing 2-phenylethyl chlorosilanes by the addition of hydrogen chlorosilane onto styrene in homogeneous systems in the presence of platinum catalysts, comprising conducting the addition reaction in the presence of benzothiazole.

2. The method of claim 1, wherein the benzothiazole is used in such amounts that the molar ratio of platinum catalyst to benzothiazole is between 1:2 and 1:50.

3. The method of claim 1, wherein the reaction is performed at temperatures between 40° and 90°, preferably between 65° and 75° C.

4. The method of claim 1, wherein the reaction is performed at an excess pressure of 2 to 6 bar.

5. The method of claim 1, wherein the styrene is injected into the hydrogen chlorosilane.

6. The method of claim 5, wherein at least 10 moles of styrene per hour are injected for every 100 moles of trichlorosilane.

7. The method of claim 1, wherein the platinum catalyst is $H_2PtCl_6$.

8. The method of claim 7, wherein the catalyst is in a homogeneous acetone solution.

9. The method of claim 1, wherein the hydrogen chlorosilane is trichlorosilane.

10. The method of claim 1, wherein the hydrogen chlorosilane is hydrogen methyldichlorosilane, hydrogen alkyl dichlorosilanes having 2 to 8 carbon atoms in the alkyl group, or dihydrogendichlorosilane.

* * * * *